US00PP37576P2

(12) United States Plant Patent
Bergman

(10) Patent No.: US PP37,576 P2
(45) Date of Patent: Aug. 11, 2026

(54) ***CHRYSANTHEMUM* PLANT NAMED 'CIDZ0125'**

(50) Latin Name: ***Chrysanthemum* x *morifolium***
Varietal Denomination: CIDZ0125

(71) Applicant: SYNGENTA CROP PROTECTION AG, Basel (CH)

(72) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 2 days.

(21) Appl. No.: 19/424,275

(22) Filed: Dec. 18, 2025

(51) Int. Cl.
*A01H 6/14* (2018.01)

(52) U.S. Cl.
USPC ..... Plt./295
CPC ..... *A01H 6/1424* (2018.05)

(58) Field of Classification Search
USPC ..... Plt./295, 289
CPC ..... A01H 5/0255
See application file for complete search history.

*Primary Examiner* — Kent L Bell
(74) *Attorney, Agent, or Firm* — Dale Skalla

(57) ABSTRACT

A new *Chrysanthemum* plant named 'CIDZ0125' particularly distinguished by its orange-bronze, single-type inflorescences, excellent flower production, compact growth and spreading plant habit, and uniform flowering with a response time of 6.5 weeks when grown under short days.

1 Drawing Sheet

Latin name of the genus and species of the plant claimed: *Chrysanthemum* x *morifolium.*

Varietal denomination: 'CIDZ0125'.

BACKGROUND OF THE NEW PLANT

The present invention comprises a new *Chrysanthemum*, botanically known as *Chrysanthemum* x *morifolium*, and hereinafter referred to by the variety name 'CIDZ0125'.

'CIDZ0125' is a product of a planned breeding program. The new cultivar has orange-bronze, single-type inflorescences, excellent flower production, compact growth and spreading plant habit, and uniform flowering with a response time of 6.5 weeks when grown under short days.

'CIDZ0125' originates as a natural whole plant mutation discovered among flowering plants of 'C1231" growing in a large outdoor field in Alva, Florida in March 2021. The parent 'C1231', was a proprietary breeding line, having light pink inflorescence color while similar to 'CIDZ0125' in all other characteristics. Compared to sibling cultivar 'CIDZ01242', (Co-pending U.S. Plant Pat. No. 19/423,222), 'CIDZ0125' produces orange-bronze inflorescences and 'CIDZ0124' produces white inflorescences.

The first act of asexual reproduction of 'CIDZ0125' was accomplished when vegetative cuttings were propagated from the initial selection in June 2021 in a saran covered field in Alva, Florida.

BRIEF SUMMARY OF INVENTION

Horticultural examination of plants grown from cuttings of the plant initiated in June 2021, and continuing thereafter, has demonstrated that the combination of characteristics as herein disclosed for 'CIDZ0125' are firmly fixed and are retained through successive generations of asexual reproduction.

'CIDZ0125' has not been observed under all possible environmental conditions. The phenotype may vary significantly with variations in environment such as temperature, light intensity and day length.

A Plant Breeder's Right for this cultivar has not yet been applied for. 'CIDZ0125' has not been made publicly available prior to the effective filing date of this application, notwithstanding any disclosure that may have been made less than one year prior to the effective filing date of this application by the inventor or another who obtained 'CIDZ0125' directly from the inventor.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawings show typical flower and foliage characteristics of 'CIDZ0125' with colors being as true as possible with an illustration of this type.

Figure 1:
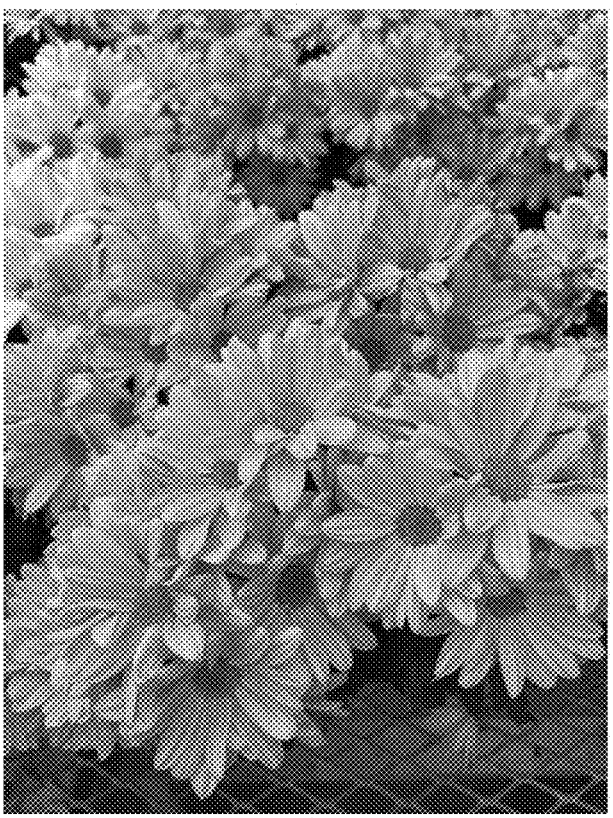

The whole plant photographic drawing, shown in FIG. 1, was taken in Gilroy, California in August 2025.

Figure 2:
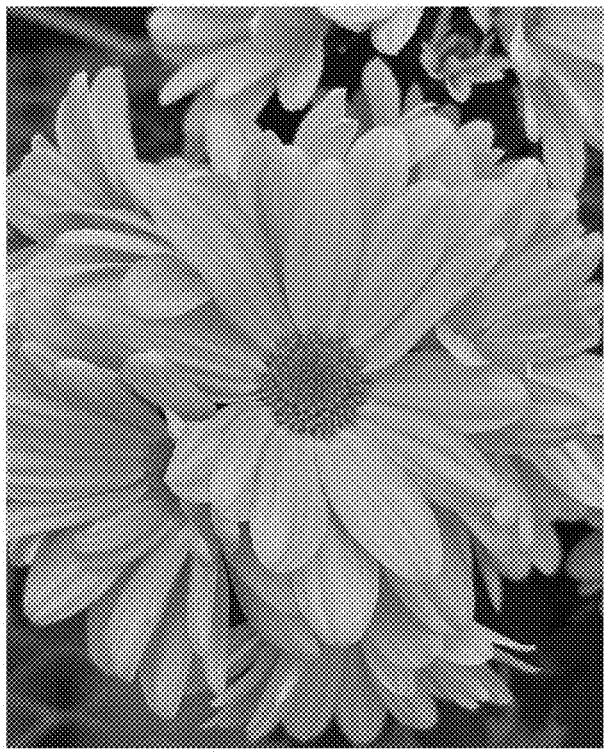

The close-up view of the inflorescence shown in FIG. 2, was taken in Gilroy, California in November 2025.

DETAILED BOTANICAL DESCRIPTION

The plant descriptions and measurements were taken indoors in Gilroy, California in November 2025 on about 11-week-old plants. Unrooted cuttings had been planted, 4 plants per pot, in 6-inch pots in September 2025. The plants were pinched and moved to short days three weeks later in September 2025 to induce flowering.

Color references are made to The Royal Horticultural Society Colour Chart (R.H.S.) 2001.

TABLE 1

DIFFERENCES BETWEEN THE NEW VARIETY 'CIDZ0125' AND A MOST SIMILAR VARIETY:

| | 'CIDZ0125' | 'CIDZ0095', U.S. Plant Pat. No. 31,325 |
|---|---|---|
| Plant height: | Shorter | Taller |
| Foliage quality: | Resists lower foliage breakdown | Lower foliage breakdown under low light conditions |
| Flowering response: | Several days faster | Several days slower |
| Flower size: | Larger | Smaller |

Plant:

*Form, growth and habit.*—Herbaceous pot-type, stems upright, freely branching, strong and moderately vigorous growth habit.

*Plant height.*—14.5-15.0 cm.

*Plant height* (*inflorescence included*).—20 cm.

*Plant width.*—34 cm.

Roots:

*Number of days to initiate roots.*—4 days at about 22 degrees C.

*Number of days to produce a rooted cutting.*—10-12 days at 22 degrees C.

*Type.*—Fine, fibrous, free branching.

*Color.*—RHS N155B but whiter.

Foliage:

*Arrangement.*—Alternate.

*Immature, leaf color, upper surface.*—Blend of RHS 137A to 138A.

*Lower surface.*—RHS 138B.

*Mature, leaf color, upper surface.*—RHS 137A.

*Lower surface.*—RHS 137C.

*Length.*—5.5-7.0 cm.

*Width.*—4.5-6.5 cm.

*Shape.*—Ovate.

*Base shape.*—Attenuate.

*Apex shape.*—Mucronulate.

*Margin.*—Lobed with some serration.

*Texture, upper surface.*—Puberulent.

*Lower surface.*—Puberulent.

*Color of veins, upper surface.*—RHS 138B.

*Color of veins, lower surface.*—RHS 138C.

*Pattern of veining.*—Pinnate.

*Petiole color.*—RHS 137A.

*Length.*—1.5-2.4 cm.

*Diameter.*—0.2-.3 cm.

*Texture.*—Puberulent.

Stem:

*Quantity of main branches per plant.*—3.

*Color of stem.*—RHS 138B.

*Length of stem.*—8-11 cm.

*Diameter.*—0.3-0.5 cm.

*Length of internodes.*—0.5-2 cm.

*Texture.*—Puberulent.

*Color of peduncle.*—In between RHS 138A and 138B.

*Length of peduncle.*—1.5-3.5 cm.

*Peduncle diameter.*—0.2 cm.

*Texture.*—Puberulent.

Inflorescence:

*Type.*—Compositae type, solitary single-type inflorescences borne terminally above foliage, ray florets arranged acropetally on a capitulum.

*Quantity of short days to flowering* (*response time*).—6.5 weeks.

*Natural season flowering.*—Not determined on this variety.

*Quantity of inflorescences per plant.*—8-18.

*Lastingness of individual blooms on the plant.*—4 weeks.

*Fragrance.*—Slightly spicy.

Bud: (just when opening/showing color)

*Color.*—Closest to RHS 158D.

*Length.*—0.5-0.6 cm.

*Width.*—0.7-0.8 cm.

*Shape.*—Oblate spheroid.

Immature inflorescence:

*Diameter.*—4-5.5 cm.

*Color of ray florets, upper surface.*—RHS 7B with an overlay of RHS 25A.

*Lower surface.*—RHS 5D.

Mature inflorescence:

*Diameter.*—8-9 cm.

*Depth.*—2-3 cm.

*Total diameter of disc.*—1.5-2 cm.

*Receptacle color.*—A mix of RHS 145A and 145B and RHS 154C.

*Receptacle height.*—0.4-0.5 cm.

*Receptacle diameter.*—0.6 cm.

Ray florets:

*Average quantity of florets.*—23.

*Color of ray florets, upper surface.*—RHS 7A with an overlay of RHS 25A.

*Lower surface.*—RHS 10C.

*Length.*—2.5-4.2 cm.

*Width.*—0.8-1.5 cm.

*Shape.*—Elliptical.

*Apex shape.*—Mucronate.

*Margin.*—Entire.

*Texture, upper surface.*—Smooth.

*Lower surface.*—Smooth.

Disc florets:

*Average quantity of florets.*—156.

*Color of florets.*—RHS 145B at the apex and RHS 154D at the base.

*Length.*—0.3-0.6 cm.

*Width.*—0.1 cm.

*Shape.*—Tubular, elongated.

*Apex shape.*—Acute, 5 pointed.

Phyllaries:

*Quantity.*—21-26.

*Color, upper surface.*—RHS 139B.

*Lower surface.*—RHS 138A.

*Length.*—0.5-0.7 cm.

*Width.*—0.3-0.5 cm.

*Shape.*—Lanceolate.

*Apex shape.*—Acute.

*Base.*—Fused.

*Margins.*—Entire; slightly papery.

*Texture, upper surface.*—Smooth.

*Lower surface.*—Puberulent.

Reproductive organs:

*Pistil.*—1, found on both types of florets.

*Length.*—0.6-0.7 cm.

*Style color.*—RHS 150C.

*Style length.*—0.5 cm.

*Stigma color.*—RHS 1C.

*Stigma shape.*—Bi-parted.

*Ovary color.*—RHS 155C but more translucent.

*Stamens.*—4, found only on the disc florets.

*Color of filaments.*—RHS 155C.
*Length filaments.*—0.4 cm.
*Anther color.*—RHS 1B.
*Anther length.*—0.1 cm.
*Anther shape.*—Oval.
*Color of pollen.*—Absent.
*Pollen amount.*—Absent.
*Fertility/seed set.*—Has not been observed to date.
*Disease/pest resistance.*—Has not been observed to date.

What is claimed is:

1. A new and distinct variety of *Chrysanthemum* plant named 'CIDZ0125' substantially as illustrated and described herein.

* * * * *